United States Patent [19]

Schurek et al.

[11] Patent Number: 4,894,150
[45] Date of Patent: Jan. 16, 1990

[54] MECHANICAL DEVICE FOR SIMPLIFYING FLUID BALANCE IN HEMOFILTRATION

[76] Inventors: Hans-Joachim Schurek, Sperlingsfeld 9; Jörg-Dieter Biela, Wilhelm-Blum-Str. 19, both of D-3000 Hanover, Fed. Rep. of Germany

[21] Appl. No.: 205,618

[22] Filed: Jun. 2, 1988

Related U.S. Application Data

[63] Continuation of Ser. No. 820,442, Jan. 17, 1986, abandoned, which is a continuation-in-part of Ser. No. 483,280, Apr. 8, 1983, abandoned.

[30] Foreign Application Priority Data

Apr. 10, 1982 [DE] Fed. Rep. of Germany ....... 3213390

[51] Int. Cl.$^4$ .............................................. B01D 13/00
[52] U.S. Cl. .................................... 210/101; 210/134; 210/321.65; 210/929
[58] Field of Search .................. 141/83; 177/112, 114, 177/158, 170, 250, 251; 210/100, 101, 110, 134, 137, 321.65, 929; 222/57, 77

[56] References Cited

U.S. PATENT DOCUMENTS

| 75,146 | 3/1868 | Forsyth et al. | 177/250 |
| 1,167,941 | 1/1916 | Shaw | 177/250 |
| 2,026,290 | 12/1935 | Teraoka | 177/170 |
| 3,242,924 | 3/1966 | Kraft et al. | 128/214 |
| 3,299,977 | 1/1967 | Melendy | 177/158 |
| 3,425,415 | 2/1969 | Gordon et al. | 128/214 |
| 3,949,744 | 4/1976 | Clarke | 210/446 X |
| 4,204,957 | 5/1980 | Weickhardt | 210/929 X |
| 4,240,408 | 12/1980 | Schael | 210/929 X |

FOREIGN PATENT DOCUMENTS

| 1566680 | 1/1971 | Fed. Rep. of Germany . |
| 2629717 | 5/1978 | Fed. Rep. of Germany ... 210/321.2 |
| 2397197 | 9/1974 | France | 210/321.3 |

OTHER PUBLICATIONS

Jensen, M. W. et al, "The Examination of Weighing Equipment", N.B.S. Handbook 94, Mar. 1, 1965, pp. 154–155.
Quellhorst, E. "Hamofiltration . . . " Medizintechnik, 101 Jg., 5/1981 pp. 224, 126–128.

Primary Examiner—W. Gary Jones
Attorney, Agent, or Firm—Peter K. Kontler

[57] ABSTRACT

A balance device for use in conjunction with a continuous fluid filter exchange system includes a balance beam stand, and a pair of beams pivotally mounted on the stand at respective levels above and below the filter. A source of substitution fluid for the exchange system is suspended from the upper beam while a reservoir for filtrate from the system is suspended from the lower beam. A supply tube devoid of pumps is provided for introducing substitution fluid from the source into the system, and a filtrate tube devoid of pumps is provided for conducting filtrate from the system to the reservoir. Automatic control means is provided on the stand for controlling the flow of fluid into the system as a function of the amount of filtrate collected in the reservoir, and the control means is mechanically coupled to the beams. The device further includes automatic shut-off for terminating the flow of filtrate to the reservoir when the source of substitution fluid becomes empty. In an alternative embodiment, the device comprises an inner frame and an outer frame with the source of substitution fluid and the reservoir being suspended from the inner frame. The inner frame is movable relative to the outer frame, and the control means is mounted so as to operate in response to relative movements of the inner and outer frames.

30 Claims, 4 Drawing Sheets

MECHANICAL DEVICE FOR SIMPLIFYING FLUID BALANCE IN HEMOFILTRATION

CROSS-REFERENCE TO RELATED APPLICATION

This application is a continuation of application Ser. No. 820,442, filed 1/17/1986, now abandoned, which is a continuation-in-part application of Ser. No. 483,280, filed 4/8/1983, now abandoned.

BACKGROUND OF THE INVENTION

The present invention relates to a mechanical device for simplifying fluid balance in a filtration system, particularly a continuous arterio-venous hemofiltration (CAVH) system. Continuous arteriovenous hemofiltration (CAVH) has become a valuable tool in the treatment of acute renal failure in critically ill patients.

In patients experiencing acute or chronic renal failure, the elimination of excess water and waste products is conventionally performed by hemodialysis. This mode of treatment is quite different from the function of natural kidneys. Hemodialysis utilizes relatively high cost, technically sophisticated, electronically controlled machines to effect this process. Connections to electricity and to pure water (deionized water or reverse osmosis water) are necessary. Moreover, association with a regular technical service is required and the procedure must be performed by specialized nurses and physicians. A standard hemodialysis treatment regimen is 3X5 hours during one week. As excess water and waste products are eliminated quite rapidly during the short treatment periods, hemodynamic instability is a common side effect. The same is generally true for mechanical hemofiltration, although there are differences in quantity.

A recently developed mode of treating patients who have acute renal failure is with continuous arterio-venous hemofiltration This treatment is directed primarily to patients who are immobilized and must be treated using a mechanical respiratory assist. By the use of this mode of treatment, some of the disadvantages of conventional therapy can be eliminated and the attendant costs reduced.

In continuous arterio-venous hemofiltration, a small capillary hemofilter is connected to both a patient's artery and vein to provide access to the patient's blood. The filter capillaries are permeable to water and non-protein bound substances up to a molecular weight of 10000 to 50000 daltons. Blood cells and protein, however, remain within the blood compartment. This treatment is intended to simulate the function of the patient's kidneys. Filtration is driven by the patients circulation without the necessity for an extracorporeal pump. Only 1 to 2% of the patient's circulation is used for this extracorporeal circulation. As the pressure gradient between the arterial and venous blood vessels is the driving force, the procedure was named continuous arteriovenous hemofiltration (CAVH). After filtration, filtrate generated is discarded and a substitute is infused into the venous line. Every hour a volume of between 500 and 1000 ml has to be manually balanced by a nurse. Manual handling of a daily fluid exchange of between 12 and 20 liters presents certain problems in patient care due to a possible imbalance.

OBJECTS AND SUMMARY OF THE INVENTION

It is an object of the invention to provide a simple and efficient method of and device for handling fluid exchange, particularly continuous fluid exchange such as CAVH.

Another object of the invention is to provide a method and a device which permit automatic fluid balance to be achieved without having to resort to manual procedures.

An additional object of the invention is to provide a method and a device which alleviate the medical and economic disadvantages of conventional hemodialysis treatments.

A further object of the invention is to provide a method and a device which can be used by the intensive care staff of a hospital with minimum training.

The preceding objects, as well as others which will become apparent as the description proceeds, are achieved by the invention.

One aspect of the invention resides in a device for equalizing the rate of flow of substitution fluid and the rate of flow of filtrate in a filtration system, particularly a continuous arterio-venous hemofiltration system, where a waste-enriched fluid, e.g., a fluid enriched in metabolic wastes, is passed through a filter, a portion of the waste-enriched fluid is removed as filtrate, and the removed portion of the waste-enriched fluid is at least partially replaced by a substitution fluid. The device comprises the following:

A. A mechanical balancing system designed to support a source of the substitution fluid at a first level above the filter, and to support a reservoir for the filtrate at a second level below the filter. The balancing system is arranged to undergo deflection in response to a difference between an instantaneous equilibrium force and the instantaneous total weight of fluid in the source and the reservoir.

B. A control unit for regulating the rate of flow of the substitution fluid from the source.

C. A mechanical linkage designed to transmit motion between the balancing system and the control unit in such a manner that the control unit changes the flow rate of the substitution fluid from the source in response to deflection of the balancing system.

According to one embodiment of the invention, the balancing system includes a vertical stand having two mechanically coupled, horizontal cross beams mounted on roller bearings. The beams are disposed at different levels, and a source or bag of substitution fluid, e.g., a 4.5 liter bag, suspended from one side of the upper beam, e.g., approximately 2 meters above the ground, is counterbalanced by a weight on the opposite side. When filtrate is introduced into a reservoir or container suspended from the lower beam below the bag of substitution fluid, a growing imbalance arises and causes opening of a control unit or tube clamp which mechanically sets the fluid substitution rate to the rate of filtration with a high degree of accuracy, e.g., ±10 ml/4.5 liter exchange. The lower beam may, for example, be mounted at a height of 76 cm above the ground while the container, e.g., of 10 liter capacity, is then suspended at a height of 42 cm. Using this arrangement, it is possible to gain additional negative pressure from the level of the filter (the level of a patient's bed in the case of a hemofilter) by locating the end of the filtrate tube directly above the container. Setting the level of the upper beam at 2 meters above the floor guarantees a hydrostatic pressure sufficiently high to enable substitution to occur even through an extra filter system.

The tube clamp may be constructed of a tube holding block in which a flexible tube segment (e.g., a silastic tube which is integrated into the infusion line) is suspended. A movable pin for tube clamping is mechanically coupled to a coupling bar serving to join the beams.

The set point of the automatic balancing system may be adjusted by an extra weight, e.g., a 650 g weight, movable along a screw constituting a prolongation of the lower beam. This permits exact adjustment of the system to compensate for small differences in the weights of the substitution fluid bags delivered by different suppliers.

To effect a negative balance, another component may be added. This may take the form of a graduated container, e.g., of 2 liter capacity, which is suspended on the same side as the counterweight and is partially filled with fluid at the end of a cycle. The graduated container may be gradually and continuously filled during an exchange using a drip infusion unit. The infusion rate then determines the negative balance. On the other hand, the graduated container may be filled prior to an exchange. If, for example, a negative balance of 2 liters is required for a 4.5 liter exchange, the graduated container is filled with 2 liters of fluid and, at the end of the exchange run, the filtrate container has 6.5 liters of fluid to balance the 4.5 liters of substitution fluid and the 2 liters of negative balance fluid.

A negative balance may also be achieved by providing one of the beams with means for positioning the substitution fluid bag or the filtrate container at any of a plurality of preselected locations along the respective beam. The positioning means may, for instance, be designed in such a manner that the negative balance can be adjusted in steps of 0.5 liter. Preferably, the positioning means is formed on the lower beam which supports the filtrate container. The positioning means may, for example, take the form of notches.

According to another embodiment of the invention, the balancing system includes a first frame, and a second frame which at least partly surrounds the first frame. One of the frames carries the other of the frames and is capable of being suspended, e.g., from a ceiling. It is preferred for the second or outer frame to carry the first or inner frame. The inner frame is then shiftable relative to the outer frame and is designed to support both the substitution fluid bag and the filtrate container. A biasing element may be disposed between the frames and functions as a counterweight. The control unit, which may again be in the form of a tube clamp, here regulates the rate of flow of substitution fluid from the bag in response to relative movements of the frames. Preferably, these relative movements are transmitted to the tube clamp via a scissors-like lever arrangement.

Once the substitution fluid bag has been emptied, it is desirable to terminate the flow of filtrate to the filtrate container. This is particularly important in the case of a patient undergoing hemofiltration. In order to insure that the flow of filtrate will not continue indefinitely when an attendant fails to realize that the substitution fluid bag is empty, a shut-off unit may be provided to automatically terminate the flow of filtrate to the filtrate container once emptying of the substitution fluid bag has occurred. The shut-off unit may, for instance, take the form of a tube clamp which is caused to pinch the tube or hose leading from the filter to the filtrate container after the substitution fluid bag is empty. In the double-beam embodiment of the invention, the tube clamp is advantageously activated by one of the beams, preferably the lower beam which supports the filtrate container.

Another aspect of the invention resides in a filtering method, particularly for use in continuous arterio-venous hemofiltration, which comprises the following steps:

A. Conveying a first fluid along a circulatory path.

B. Filtering the first fluid in a predetermined portion of the circulatory path to generate a filtrate.

C. Withdrawing the filtrate from the predetermined portion of the circulatory path and admitting the filtrate into a reservoir. The withdrawing and admitting step is performed at least in part gravitationally and without passing the filtrate through a pump.

D. Withdrawing a substitution fluid from a source of the latter and introducing the substitution fluid into the circulatory path. The withdrawing and introducing step is performed at least in part gravitationally and without passing the substitution fluid through a pump.

E. Regulating the introduction of the substitution fluid into the circulatory path in dependence upon differences between an instantaneous equilibrium force and the instantaneous total weight of fluid in the source and the reservoir. The regulating step is performed in such a manner that the rate of introduction of the substitution fluid into the circulatory path at least approximates the rate of withdrawal of the filtrate from such path.

Heretofore, a recurrent problem in continuous arterio-venous hemofiltration was the manual handling of a daily fluid exchange of between 12 and 20 liters. With the method and device of the invention, substitution bags and containers need only be changed once during each nursing shift (i.e., three times every 24 hours). The balance device is at least as safe as that of drip infusion systems. After a short training period, the staff of an intensive care unit may handle the device without experiencing any problems. Additionally, the present balance device and method avoid the risks of a manual balance procedure and its associated costs. Even if two devices are used in parallel, costs are dramatically lower than those of conventional treatment modes (hemodialysis and mechanical hemofiltration). Moreover, the method and device may, with minor modifications, also be used for different fluid balance problems such as forced diuresis for the treatment of intoxification, gut lavage, arteriovenous plasma filtration and continuous cyclic peritoneal dialysis, as well as in chemical or technical processes.

The novel features which are considered as characteristic of the invention are set forth in particular in the appended claims. The improved arrangement, itself, however, both as to its construction and the mode of assembling the same, together with additional features and advantages thereof, will be best understood upon perusal of the following detailed description of certain specific embodiments with reference to the accompanying drawings.

DESCRIPTION OF THE PREFERRED EMBODIMENTS

Figures 1, 2:
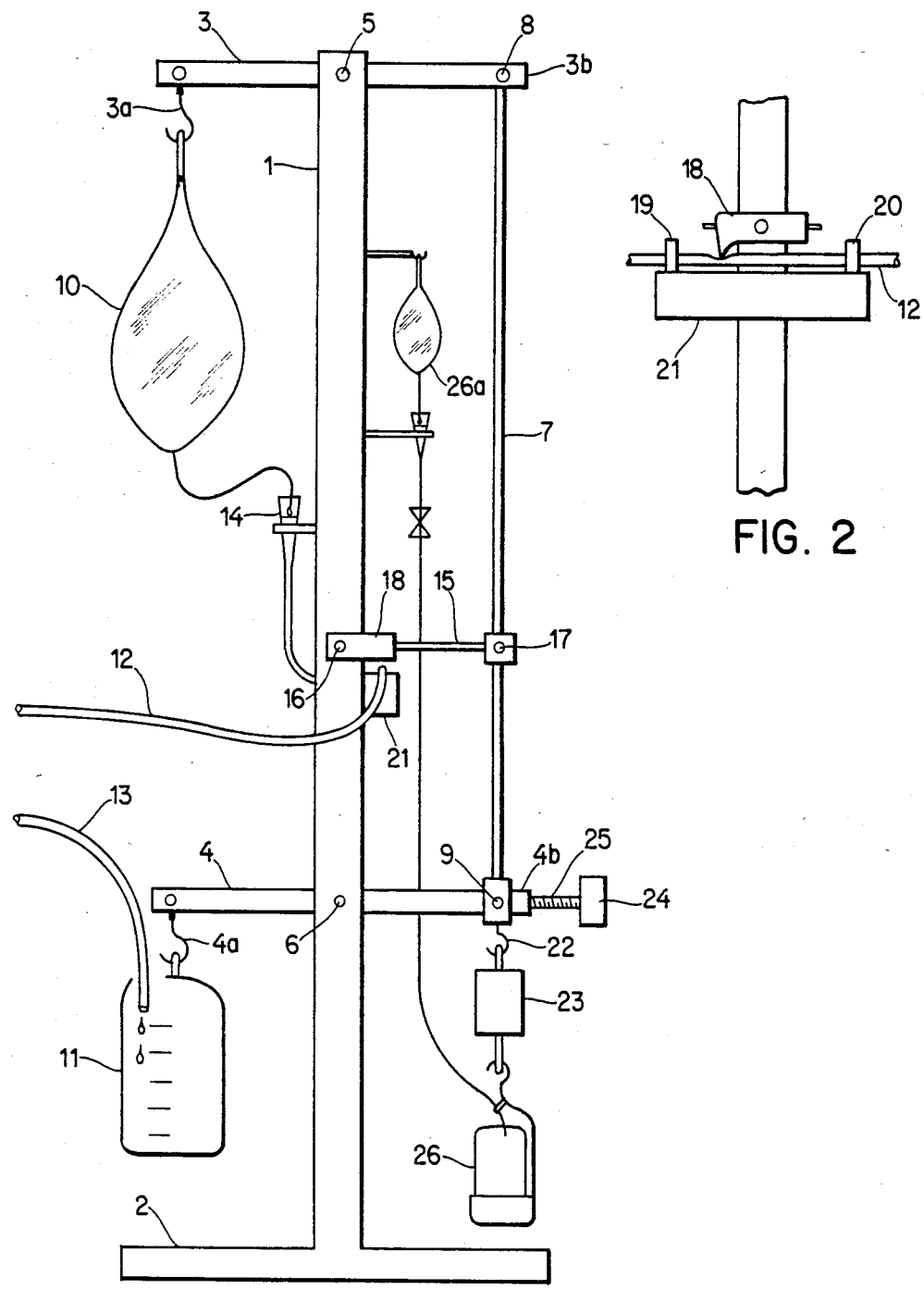
FIG. 1 is a side elevational view of a double-beam balance embodiment of the subject invention.
FIG. 2 is an enlarged view of a tube clamp included in FIG. 1.

Referring first to FIG. 1, there is shown a vertical stand 1 having a base 2, and horizontal upper and lower cross beams 3 and 4, respectively, which are pivotally mounted on the stand 1 by roller bearings 5 and 6, respectively. The ends 3b and 4b of the upper and lower beams 3 and 4 have joints 8 and 9 which are connected by a rod 7. A hook 3a is provided at the end of the upper beam 3 opposite the end 3b, and a substitution bag 10 is suspended from the hook 3a. A graduated container 11 is similarly suspended from a hook 4a provided at the end of the lower beam 4 opposite the end 4b, and the graduated container 11 is adapted to take up filtrate. An infusion line depends from the bag 10 and enters a drip chamber 14 connected to a conduit or tube 12.

A tube or conduit 13 leading from a hemofilter is mounted on a stand (not shown) in such a manner as to be adjustable and hang freely in a relatively wide opening of the graduated container 11. On the stand 1, there is a tube clamp including a clamp board 21 over which the tube 12 is extended through a pair of guides 19 and 20. The clamp board 21 may be mounted horizontally as shown, for example, in FIG. 2, or may be mounted vertically. A single-armed lever 15 has a first end which is pivotally connected with the connecting rod 7 via a pivot pin 17. The other end of the lever 15 is secured to or cooperates with a clamping bracket 18 which is mounted on the stand 1 by means of a pivot pin 16. In order to reduce forces upon the tube 12 in one end position of the balance, the lever 15 may be fabricated from spring steel or, alternatively, another clamping mechanism may be used, e.g., a mechanism having a vertical tube bed as well as a horizontally directed clamping pin which cooperates with a movable vertical arm of the bracket 18. Such movable vertical arm may be connected with the bracket 18 at the pivot pin 16 via a torque spring in a Teflon ® chamber. This optimizes the leverage for the clamping function.

A hook 22 is provided on the lower cross beam 4, and a counterweight 23 for the substitution bag 10 is suspended from the hook 22. In order to precisely adjust the starting point of the tube clamp 18,21 an extra weight 24 is adjustably positioned on a screw thread 25 forming an extension of the lower beam 4. It is therefore possible to adjust the moment or torque precisely to the point where the drip rate from the substitution bag 10 equals the drip rate of the filtrate. Below the counterweight 23 there is an extra container 26 which may be calibrated. This makes it possible to obtain a negative balance of fluid exchange.

When starting the present device under clinical conditions in order to perform continuous arterio-venous hemofiltration, the tube carrying the filtrate is mounted above the filtrate container 11, and the tube clamp 18,21 is adjusted by means of the adjusting weight 24. In the case of an overhydrated patient where acute withdrawal of fluid from the patient is necessary, the negative balance container 26 is filled with water to the desired range. The tube clamp 18,21 then remains closed until the amount of filtrate corresponds exactly to the amount of fluid in the negative balance container 26. The device thereupon operates in a steady state condition moving the mass point slowly from the upper beam 3 to the lower beam 4. If a continuous negative balance is desired, a drip infusion tube mounted on the vertical stand 1 and connected with a source 26a of an appropriate fluid such as water is led into the negative balance container 26. The drip infusion rate, which may be set by a valve on the drip infusion tube, then determines the negative balance.

The device may be constructed using a single beam, and the substitution bag 10 may then be bridged by a frame which carries a mounting pin for the filtrate container 11.

Figure 3:
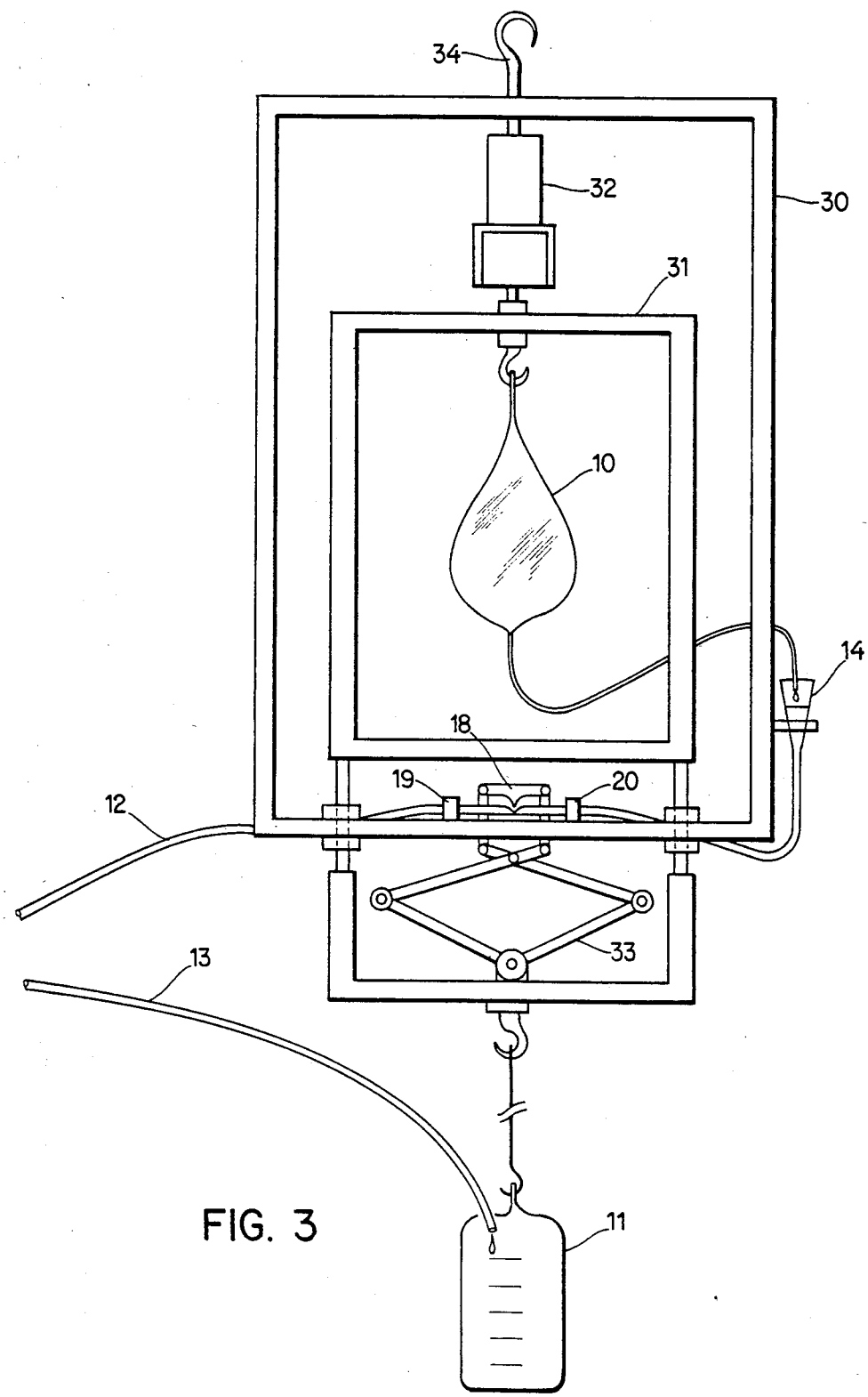
FIG. 3 is a side elevational view of a spring balance embodiment of the subject invention.

An alternative embodiment, which is shown in FIG. 3, includes a hanging double frame unit having an outer frame 30 and an inner frame 31. The counterweight 23 of FIG. 1 is replaced by a biasing element 32 such as a spring balance or a pneumatic cylinder provided between the frames 30 and 31. The substitution bag 10 and the filtrate container 11 are suspended from the inner frame 31. The movement of frames 30 and 31 relative to one another may be used to regulate the clamping bracket 18. In order to transfer the frame movements to the clamping bracket 18, a scissors-like or collapsible lever arrangement 33 is provided. When the sum of the weights, i.e., the weight of the substitution fluid plus the weight of the filtrate increases, the clamping bracket 18 opens setting the fluid substitution rate to the rate of filtration. A negative balance may be effected using a roller arrangement which lifts the inner frame 31 when the weight is increased by addition of a negative balance container (not shown). The device of FIG. 3 may be hung from the ceiling via a hook 34.

Figure 4:
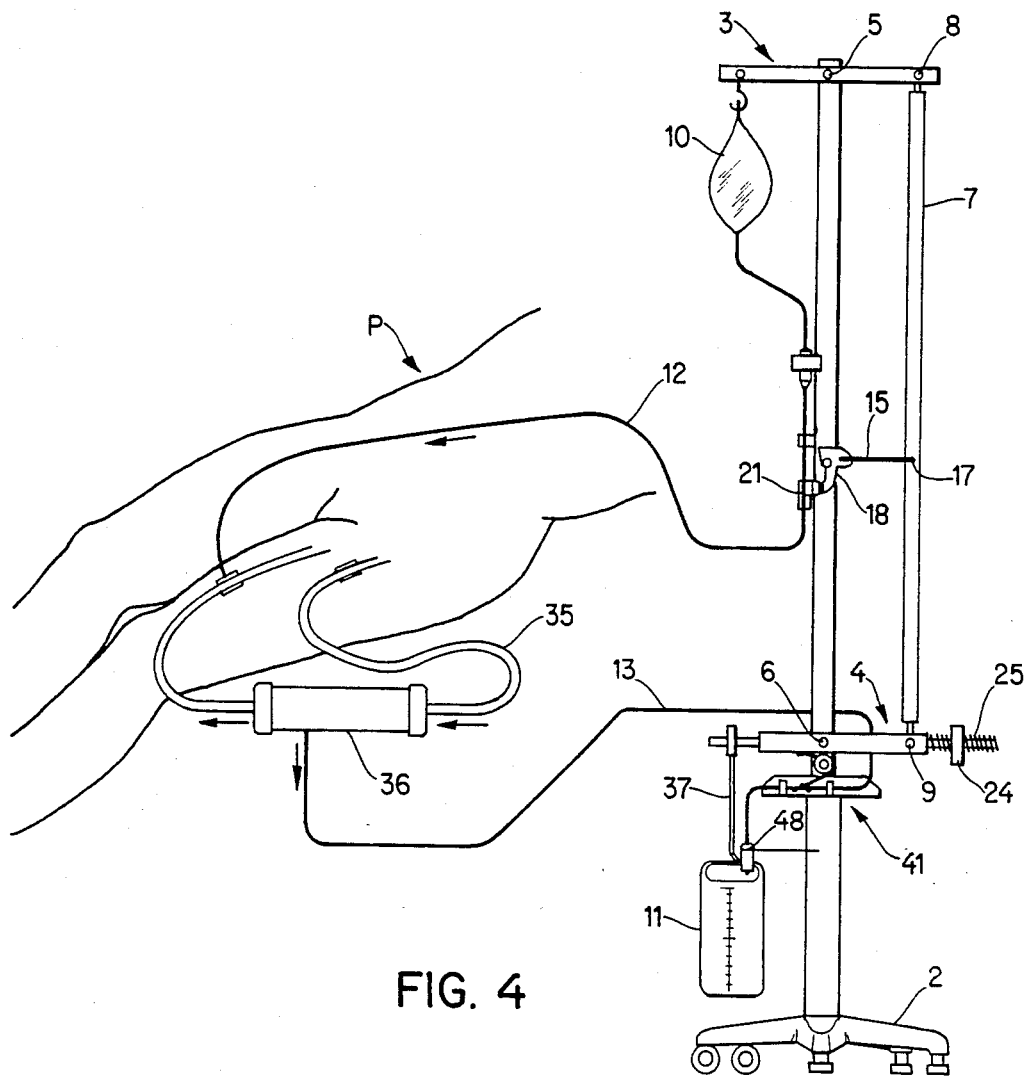
FIG. 4 is a side elevational view of another double-beam balance embodiment of the subject invention.

FIG. 4 shows another embodiment of a doublebeam balance according to the invention being applied for continuous arterio-venous hemofiltration of a patient P. The balance of FIG. 4 generally resembles that of FIG. 1 but differs therefrom in certain respects.

The major differences between the balances of FIGS. 1 and 4 are outlined below. However, before describing these differences, it is noted that FIG. 4 illustrates how a balance in accordance with the invention is connected with a patient such as the patient P.

The patient P is connected to a hemofilter 36 by means of a tube 35 leading into and out of the hemofilter 36. The tube 35 has a first end which is inserted in an artery of the patient P and a second end which is inserted in a vein of the patient P. The tube 35 and hemofilter 36, together with the circulatory system of the patient P, then define a circulatory path for the patient's blood. As illustrated by the horizontal arrows adjacent to the tube 35, blood rich in metabolic wastes enters the hemofilter 36 on the right while filtered blood leaves the hemofilter 36 on the left. A portion of the blood is withdrawn from the hemofilter 36, and hence from the circulatory path, as filtrate. This is indicated by the downwardly pointing arrow adjacent to the hemofilter 36. The filtrate is conducted to the filtrate container 11 by means of the filtrate tube or line 13 which is connected with the hemofilter 36.

The portion of the blood removed from circulation as filtrate is partially or entirely made up by the substitution fluid as indicated by the arrow adjacent to the substitution fluid tube or line 12 leading away from the substitution bag 10. The end of the substitution fluid tube 12 remote from the substitution bag 10 is hooked into the circulatory tube 35 downstream of the hemofilter 36, that is, the substitution bag 10 is connected for hemofiltration in a postdilution mode. However, if the substitution bag 10 is arranged at a height sufficient to overcome the mean arterial blood pressure, the end of the substitution fluid tube 12 remote from the substitution bag 10 may be hooked into the circulatory tube 35 upstream of the hemofilter 36, i.e., the substitution bag 10 may be connected for hemofiltration in a predilution mode.

It is worthwhile here to briefly review the state of the art for treating patients with terminal renal failure. Thus, the following treatments are currently available to physicians:

A. Mechanical peritoneal dialysis.
B. Mechanical hemodialysis.
C. Mechanical hemofiltration.
D. Mechanical hemodiafiltration.
E. Continuous ambulatory peritoneal dialysis.
F. Continuous arterio-venous hemofiltration.

Treatments (B)–(D) are all performed mechanically which has the disadvantage of causing damage to the blood. Furthermore, while the natural kidney operates continuously, each of the treatments (A)–(D) is intermittent.

In mechanical hemodialysis, hemofiltration and hemodiafiltration, blood must be actively pumped at rates of 200–500 ml/min. This leads to the drawback that expensive monitoring is required. Thus, a negative pressure monitor is mandatory in the arterial line of the extracorporeal circuit as is pressure monitoring of the venous line. In addition, an electromagnetic security clamp connected with an ultrasonic air detector must be placed in the venous line.

Moreover, in mechanical hemodialysis, the dialysis fluid, which is used to wash out metabolic waste products and excess water, must be prepared from purified water, i.e., water obtained from an ion exchange column or by reverse osmosis, and a salt concentrate. This fluid must then be monitored for salt content, i.e., conductivity, and temperature. Due to the high pressures involved, a blood leak detector also is mandatory.

In mechanical hemofiltration, blood is pumped through a highly water permeable hemofilter where blood water is removed as filtrate. The lost blood water is at least partially replaced by warm substitution fluid. In order to accurately regulate replacement of the blood water by the substitution fluid, the filtrate and the substitution fluid in commercially available apparatus are weighed by mechano-electrical transducers. A microprocessor then establishes the parameters necessary to achieve the desired replacement conditions. The use of mechano-electrical transducers and a microprocessor further adds to the cost of commercially available apparatus for mechanical hemofiltration.

Mechanical hemodiafiltration also involves great expense because it is a combination of hemodialysis and hemofiltration.

In contrast to treatments (A)–(D), treatments (E) and (F), namely, continuous ambulatory peritoneal dialysis and continuous arterio-venous hemofiltration, are continuous processes. As compared to treatments (A)–(D), treatments (E) and (F) have the further advantage that they can be performed without incurring great technical expense. This is particularly important for continuous arterio-venous hemofiltration, or CAVH, which is currently restricted mainly to patients suffering from acute renal failure within a syndrome of multiple organ failure. The reason is that such patients are generally confined in intensive care units for which cost reduction is a major consideration. Reduced technical expense is less of a factor for continuous ambulatory peritoneal dialysis, or CAPD, because the patient generally performs this procedure himself or herself.

In CAVH, blood withdrawn from a patient's artery is conducted through a small hemofilter and then introduced into one of the patient's veins. While mechanical pumps are used to circulate the blood in mechanical hemodialysis, hemofiltration and hemodiafiltration, CAVH employs the patient's own heart for blood circulation, i.e., 1 to 2% of the blood pumped by the heart. Consequently, pressure monitoring as in the mechanically driven blood purification techniques is unnecessary in CAVH because there is no risk of air embolism (all pressures are above atmospheric pressure). Although CAVH is less effective than intermittent mechanical hemofiltration when considered on an hourly basis, it can be continuously used 24 hours per day since there are no mechanical pumps which damage the blood as in mechanical purification techniques. Accordingly, on a weekly basis, CAVH is more effective than the three weekly treatments of intermittent mechanical hemofiltration normally used in cases of terminal chronic renal failure.

CAVH has an additional advantage worth mentioning. Thus, there are certain patients who have circulatory problems which are characterized by rapid fluid loss and thereby prevent treatment using conventional intermittent blood purification techniques. Such patients are, however, treatable by means of CAVH.

Inasmuch as CAVH is currently used mainly for patients suffering from acute renal failure within a syndrome of multiple organ failure, a precise balance between the substitution fluid and the blood water removed from a patient is essential. The prior art attempts to obtain such a balance manually via an attendant such as a nurse. However, manual balancing of fluid has the drawback that the risk of creating an imbalance is very great. While it is true that intermittent mechanical hemofiltration permits good fluid balance to be achieved, this procedure has the disadvantages outlined above as well as the following additional disadvantages: (i) since fluid withdrawal occurs only intermittently, i.e., during the 3 to 4 hour treatment period per 24 hours, there are ups and downs in fluid status; (ii) there are ups and downs in blood chemistry; and (iii) specialized attendants including technicians, nurses and physicians must be available.

As explained earlier, the balance device of the invention eliminates the need for manual balancing during CAVH thereby greatly reducing the risk of an imbalance. A significant advantage of the balance device is that the balancing system is mechanical so that a balance is obtained purely by gravity without employing a source of external power such as electricity. Similarly, the linkage, i.e., the lever 15 or lever arrangement 33, between the balancing system and the clamping bracket 18 is mechanical. Again, this allows the clamping bracket 18 to be operated without an external source of power.

FIG. 4 illustrates that the flow of fluid to and from the balance device of the invention may likewise occur without an external power source. Thus, the balance device is designed such that the substitution bag 10 is supported at a level above, and the filtrate container 11 is supported at a level below, the hemofilter 36. Fluid flow from the substitution bag 10 to the patient P lying at the level of the hemofilter 36 can therefore proceed entirely by gravity without any mechanical assist, and the substitution tube 12 is correspondingly devoid of pumps. Similarly, fluid flow from the hemofilter 36 to the filtrate container 11 is able to take place by gravity, and the filtrate tube 13 is accordingly also devoid of pumps. In practice, the blood pressure of the patient P will assist in conveying the filtrate from the hemofilter 36 to the filtrate container 11.

As mentioned earlier, the balance device of FIG. 4 differs from that of FIG. 1 in certain respects. One difference between the balance devices is that the clamp board 21 in FIG. 4 is mounted vertically rather than horizontally. Another difference is that the counterweight in FIG. 4 is constituted by or integrated within the connecting rod 7 which may, for example, have a square cross section.

Figure 5:
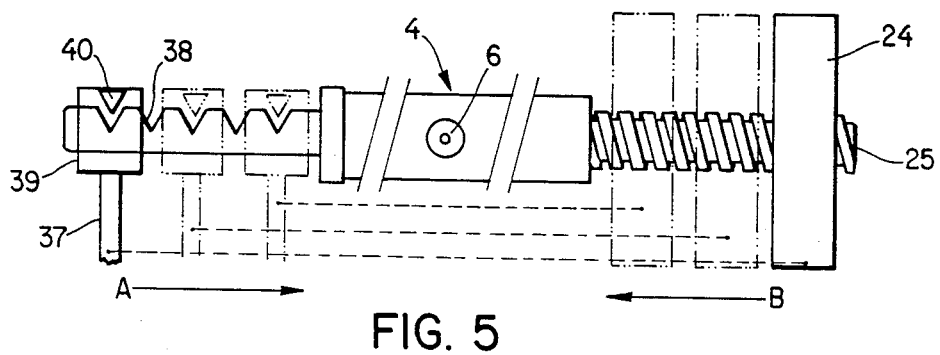
FIG. 5 is an enlarged view showing a detail of one of the beams included in FIG. 4.

In the balance device of FIG. 1, a negative balance is achieved via the extra container 26. As illustrated in FIG. 5, the balance device of FIG. 4 employs a different system for obtaining a negative balance.

FIG. 5 shows that the left-hand arm of the lower beam 4, which supports the filtrate container 11, is formed with a series of notches 38. The filtrate container 11 is carried by a bar 37 having an enlarged head 39. The head 39 is provided with a protuberance 40 which is designed to be received in the notches 38. This arrangement permits the filtrate container 11 to be positioned at any of a plurality of preselected locations along the lower beam 4. Each of the preselected locations or notches 38 corresponds to a specific negative balance including one notch 38 which corresponds to zero negative balance. The positions of the notches 38 may, for example, be selected in such a manner as to enable the negative balance to be changed from 0 to −2 liters in increments of 0.5 liter.

As illustrated by the phantom lines in FIG. 5, the imbalance created by shifting the filtrate container 11 in the direction of the arrow A may be compensated for by shifting the adjusting weight 24 in the direction of the arrow B, and vice versa. FIG. 5 also illustrates the relationship between negative balance and the positions of the notches 38 in the form of a plot of liters of filtrate per unit of substitution fluid versus length of lever arm. The number of liters of filtrate per unit of substitution fluid is plotted on the ordinate and represents the negative balance while the length of the lever arm is plotted on the abscissa and represents the positions of the notches 38. It will be observed that the relationship between negative balance and positions of the notches 38 is hyperbolic.

The balance devices of FIGS. 1 and 4 operate on the principle that the sum of the products of moment arm and weight is the same for the upper beam 3 and the lower beam 4. The positions of the notches 38 are accordingly calculated from the law of moments so as to maintain the products of moment arm and weight constant as seen in the plot of FIG. 5.

The system of FIG. 1 for obtaining a negative balance may be combined with that of FIG. 4. Thus, the extra container 26 of FIG. 1 may be suspended below the connecting rod 7 of FIG. 4 while the source 26a of negative balance fluid, as well as the drip infusion tube, shown in FIG. 1 may be mounted on the stand 1 of FIG. 4.

The balance device of FIG. 4 is further provided with a security arrangement 41 which automatically terminates the flow of filtrate to the filtrate container 11 in the event that the substitution bag becomes empty and this goes unnoticed by the attendant or attendants. The security arrangement 41 is illustrated in FIGS. 6a and 6b.

Figure 6A:
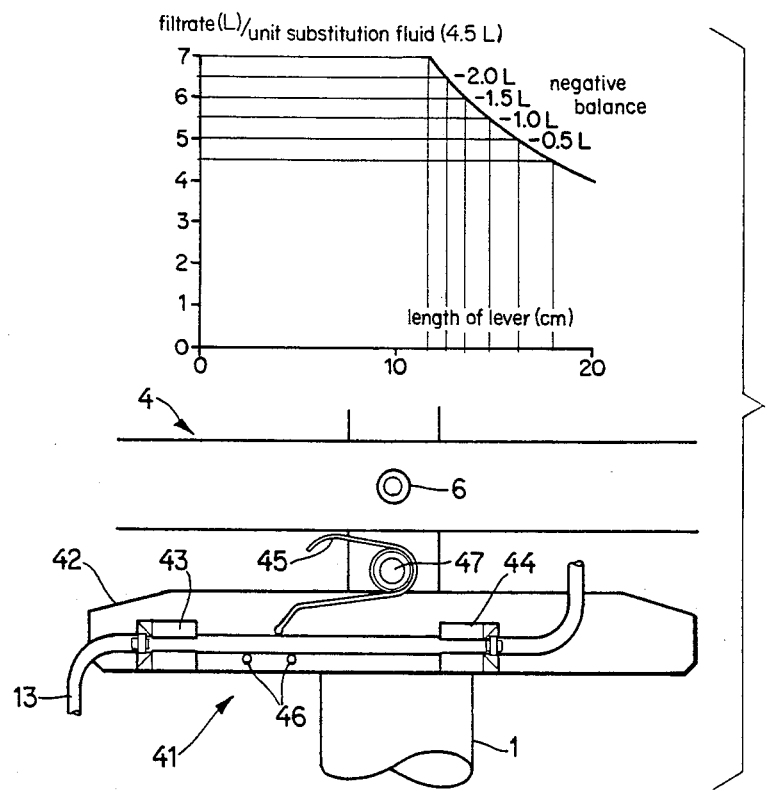
FIG. 6a is an enlarged view showing a tube clamp included in FIG. 4 in an open position.
Figure 6B:
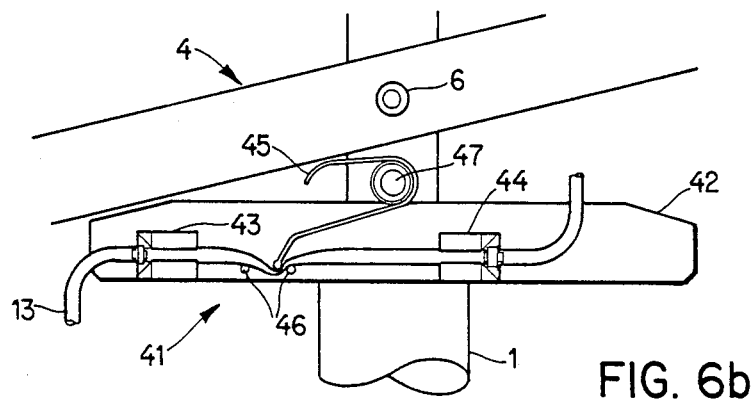
FIG. 6b is an enlarged view showing the tube clamp of FIG. 6a in a closed position.

Referring to FIGS. 6a and 6b, the security arrangement 41 is seen to include a support or bracket 42 which is arranged below the lower beam 4 and has a pair of guides 43 and 44 for the filtrate tube 13. Two spaced pins 46 are secured to the bracket 42 and underlie a segment of that portion of the filtrate tube 13 which is located between the guides 43,44. The security arrangement 41 further includes a torsion spring 45 which is mounted on a peg 47 projecting from the stand 1. The torsion spring 45 has an upper and a lower leg, and the upper leg is located adjacent to the underside of the lower beam 4. The lower leg of the torsion spring 45 is arranged such that the end of the lower leg is disposed above and adjacent to the segment of the filtrate tube 13 between the pins 46.

As long as the substitution bag 10 contains fluid and the balance device is operating normally, the lower beam 4 and the torsion spring 45 are essentially in the position of FIG. 6a and unrestricted flow of filtrate through the filtrate tube 13 occurs. However, if the substitution bag 10 becomes empty and this goes unnoticed, filtrate continues to enter the filtrate container 11 without a compensating loss of fluid from the substitution bag 10. This creates an imbalance which causes the lower beam 4 to tilt to the position of FIG. 6b. As the lower beam 4 tilts, it pushes down on the torsion spring 45 thereby causing the latter to rotate counterclockwise. The end of the lower leg of the torsion spring 45 then pinches the filtrate tube 13 against one of the pins 46 (the right-hand pin 46 in FIG. 6b) so that the filtrate tube 13 is clamped and filtrate can no longer flow to the filtrate container 11.

The amount of filtrate required to cause clamping of the filtrate tube 13 after the substitution bag 10 has been emptied is relatively small. For instance, 160–200 ml of overflow of filtrate may be required to cause clamping of the filtrate tube 13 when the negative balance is zero. Generally, the amount of overflow filtrate will increase somewhat with, and in proportion to, increasing negative balance.

As illustrated in FIG. 4, a graduated plastic container 48, e.g., a 20 ml syringe, having an outlet which can be closed may be mounted at the discharge end of the filtrate tube 13. By closing the outlet of the container 48 for a predetermined interval and measuring the amount of filtrate which enters the container 48, it is then possible to determine the rate of filtration.

A commercial infusion control unit may be used instead of the simple plastic container 48. In this case, a weight transducer is interposed between the substitution bag 10 and the hook from which it is suspended. The weight of the transducer may be compensated for by an appropriate counterweight, e.g., a 400 g counterweight. Such an arrangement permits the amount of substitution fluid which has been used, as well as the amount of fluid being filtered per unit of time, to be electronically calculated and displayed on a screen. Moreover, an alarm can be programmed to be activated when a preselected quantity, e.g., 4.5 liters, of substitution fluid has been discharged into the patient P. Although not necessary for operation of the balance device, this arrangement makes it possible to obtain a continuous balance display for control purposes.

When using a commercial infusion control unit which continuously records the amount of substitution fluid used, it is further possible to read the amount of filtrate from a simple table.

In the balance device of the invention, the substitution fluid is not pumped to the balancing system. Rather, a vessel such as the substitution bag 10 containing the substitution fluid is placed on the balancing system. Generally, the amount of substitution fluid in the vessel will be equal to that required for one exchange, e.g., 4.5 liters.

In an in vitro test, the accuracy of the balance device according to the invention was ± 10 ml for a 4.5 liter exchange performed with zero negative balance. With a negative balance of −2 liters, the accuracy was better than ±20 ml for an exchange cycle.

The method and device of the invention enable the simplicity of CAVH to be preserved while at the same time eliminating the need for risky manual balancing. Furthermore, the method and device are capable of maintaining sterility at relatively little expense as is desirable for single-use systems. The method and device according to the invention also enable a high degree of safety to be achieved and may be readily used by the nursing staff of an intensive care unit following brief instruction.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

We claim:

1. A device for equalizing the rate of flow of substitution liquid and the rate of flow of filtrate in a filtration system, where a waste-enriched liquid is filtered, a portion of the waste-enriched liquid is removed as filtrate, and the removed portion of the waste-enriched liquid is at least partially replaced by the substitution liquid, said device comprising: a filter for waste-enriched liquid, said filter including an inlet means in communication with means defining a supply of the waste-enriched liquid, a first outlet means in communication with means defining a source of substitution liquid, and a second outlet means in communication with means defining a reservoir for the filtrate; a mechanical balancing system including a stand, means provided on said stand for supporting the source of the substitution liquid at a first level above the filter, and means on said stand for supporting the reservoir for the filtrate at a second level below the filter, said balancing system undergoing deflection in response to a difference between an instantaneous equilibrium force and the instantaneous total weight of the liquid in the source and the reservoir on the respective supporting means; a control unit provided on said stand at a third level between said first and second levels and including means for regulating the rate of flow of the substitution liquid from the source on the respective supporting means to the reservoir for the filtrate; a counterweight connected to each of said supporting means to perform movements jointly with the source and the reservoir; and a mechanical linkage having means for mechanically transmitting motion between said balancing system and said control unit in such a manner that said control unit changes the flow rate of the substitution liquid from the source on the respective supporting means in response to deflection of said balancing system.

2. The device of claim 1, wherein said supporting means comprise support means, pivot means journalled in said support means, and beam means for supporting the source and the reservoir, said beam means being pivotally mounted on said pivot means.

3. The device of claim 2, wherein said beam means comprises a pair of substantially parallel beams one of which has means for carrying the source and the other of which has means for carrying the reservoir.

4. The device of claim 3, wherein each of said beams has a first arm which projects to one side of said pivot means, and a second arm which projects to the opposite side of said pivot means, said first arm of said one beam constituting said means for carrying the source and the first arm of said other beam constituting the means for carrying the reservoir, and said balancing system including connecting means connecting said second arms for deflection with one another.

5. The device of claim 4, wherein said counterweight is arranged to act on said second arms.

6. The device of claim 4, wherein said linkage comprises a lever which is coupled to said beams.

7. The device of claim 6, wherein said control unit comprises a tube clamp.

8. The device of claim 7, wherein said lever has a first end which is pivotally connected with said connecting means, and a second end which is arranged to operate said tube clamp in response to deflection of said beams.

9. The device of claim 4, wherein said balancing system comprises moment adjusting means.

10. The device of claim 9, wherein said moment adjusting means comprises a screw in alignment with one of said beams and projecting from the second arm thereof, and an adjusting weight in mesh with said screw.

11. The device of claim 4, wherein said balancing system comprises means for effecting a negative balance.

12. The device of claim 11, wherein said effecting means comprises a container suspendible from said second arms.

13. The device of claim 12, comprising drip infusion means opening into said container so as to obtain a continuous negative balance.

14. The device of claim 13, wherein said drip infusion means is mounted on said support means.

15. The device of claim 13, wherein said effecting means further comprises means on one of said first arms for positioning the source or the reservoir at any of a plurality of preselected locations along said one first arm.

16. The device of claim 11, wherein said effecting means comprises means on one of said first arms for positioning the source or the reservoir at any of a plurality of preselected locations along said one first arm.

17. The device of claim 16, wherein said positioning means comprises a plurality of notches in said one first arm each of which is disposed at one of said preselected locations.

18. The device of claim 17, wherein said one first arm is the first arm of said other beam.

19. The device of claim 4, wherein said connecting means comprises a rod which is pivotally connected with each of said second arms.

20. The device of claim 4, comprising shut-off means for automatically terminating the flow of filtrate to the reservoir in response to emptying of the source of substitution fluid.

21. The device of claim 20, wherein said shut-off means comprises a tube clamp.

22. The device of claim 20, wherein one of said beams has means for activating said shut-off means.

23. The device of claim 22, wherein said activating means is provided on said other beam.

24. The device of claim 1, wherein said counterweight constitutes a means for generating the equilibrium force.

25. The device of claim 1, comprising shut-off means for automatically terminating the flow of filtrate to the reservoir in response to emptying of the source of substitution fluid.

26. The device of claim 1, wherein said balancing system comprises means for effecting a negative balance.

27. The device of claim 1, comprising a first conduit establishing communication between said source and the filter, and a second conduit establishing communication between the filter and said reservoir, said conduits being devoid of pumps.

28. The device of claim 27, said filter being arranged in a circulatory path; and wherein said first conduit is connected with said path downstream of said filter.

29. The device of claim 27, said filter being arranged in a circulatory path; and wherein said first conduit is connected with said path upstream of said filter.

30. The device of claim 27, said second conduit having an outlet end for the discharge of filtrate into said reservoir; and wherein the level of said outlet end is adjustable.

* * * * *